(12) United States Patent
Lamb et al.

(10) Patent No.: US 9,649,513 B2
(45) Date of Patent: May 16, 2017

(54) AEROSOL DISPENSER (75) Inventors: John David Lamb, Pewsey (GB); Martin Christopher Bunce, Pewsey (GB); Alexander James Peacop, Devizes (GB); Bruce Cummings, New York, NY (US); William John Davis, Bath (GB); Barbara Porter, Hillsborough, NJ (US)

(73) Assignee: COLGATE—PALMOLIVE COMPANY, New York, NY (US)

( * ) Notice: Subject to any disclaimer, the term of this patent is extended or adjusted under 35 U.S.C. 154(b) by 2144 days.

(21) Appl. No.: 12/294,321

(22) PCT Filed: Mar. 23, 2007

(86) PCT No.: PCT/US2007/064795
§ 371 (c)(1),
(2), (4) Date: Jun. 16, 2009

(87) PCT Pub. No.: WO2007/112310
PCT Pub. Date: Oct. 4, 2007

(65) Prior Publication Data
US 2009/0297460 A1    Dec. 3, 2009

Related U.S. Application Data (60) Provisional application No. 60/785,611, filed on Mar. 24, 2006.

(51) Int. Cl.
*A61K 8/55*        (2006.01)
*A61Q 11/00*       (2006.01)
(Continued)

(52) U.S. Cl.
CPC .............. *A61Q 11/00* (2013.01); *A61K 8/896* (2013.01); *B65D 83/205* (2013.01)

(58) Field of Classification Search
CPC ....... B65D 83/205; A61Q 11/00; A61K 8/896
(Continued)

(56) References Cited

U.S. PATENT DOCUMENTS

| 2,735,590 A | 2/1956 | Ayres |
| 2,753,214 A | 7/1956 | Abplanalp |

(Continued)

FOREIGN PATENT DOCUMENTS

| CL | 1219-01 | 5/2001 |
| EM | 000263793-0001 | 12/2004 |

(Continued)

OTHER PUBLICATIONS

International Search Report and Written Opinion in International Application No. PCT/US07/064795, mailed Sep. 4, 2007.

*Primary Examiner* — J. Casimer Jacyna (57) ABSTRACT

An aerosol container has a positive actuating structure. The aerosol container is comprised of a body section and a dispensing section. The body section has an aerosol container with a valve at an end that is adjacent the dispensing section. The dispensing section has an enclosing unit and an actuating unit with an actuating channel to receive the finger of a person to actuate the actuating unit. The actuating unit fits into the enclosing unit. The actuator channel extends through the dispensing section, at least part of the lower part of the actuator channel being flexible and in contact with the valve of the aerosol container. The actuator channel can be entirely of a flexible material which directly contacts the aerosol valve or be a part of a semi-rigid to rigid material which directly contacts the aerosol valve. Upon depressing the actuator channel the aerosol valve is actuated and product flows from the body section through the dispensing section to a dispensing aperture.

16 Claims, 7 Drawing Sheets

(51) Int. Cl.
*B65D 83/14* (2006.01)
*B65D 83/20* (2006.01)
*A61K 8/896* (2006.01)

(58) Field of Classification Search
USPC ...... 222/182, 402.12, 402.13, 402.1, 402.24; D9/682, 684–694
See application file for complete search history.

(56) References Cited

U.S. PATENT DOCUMENTS

| | | |
|---|---|---|
| 2,954,904 A | 10/1960 | Potoczky |
| 2,963,265 A | 12/1960 | Goodspeed, Jr. |
| 3,089,624 A | 5/1963 | Micallef |
| 3,199,741 A | 8/1965 | Lehmann |
| D205,552 S | 8/1966 | Meyers |
| 3,312,723 A | 4/1967 | Anderson et al. |
| 3,317,092 A | 5/1967 | Jurasek |
| D216,248 S | 12/1969 | Hills |
| 3,510,029 A | 5/1970 | Doyle |
| D219,333 S | 12/1970 | Doblin |
| D220,941 S | 6/1971 | Usen |
| 3,610,479 A | 10/1971 | Venus, Jr. |
| D224,200 S | 7/1972 | Kretz |
| 3,712,515 A * | 1/1973 | Corll .................. 222/182 |
| 3,749,286 A | 7/1973 | Douglas |
| 3,785,528 A | 1/1974 | Mandeltort |
| 3,792,802 A | 2/1974 | Gores |
| 4,203,552 A | 5/1980 | Hayes |
| 4,277,004 A | 7/1981 | Barlics |
| 4,792,062 A | 12/1988 | Goncalves |
| D308,474 S | 6/1990 | Seager |
| 4,978,035 A | 12/1990 | Morane et al. |
| 4,995,417 A | 2/1991 | Naku |
| D317,253 S | 6/1991 | Seager |
| 5,070,611 A | 12/1991 | Derin et al. |
| D324,491 S | 3/1992 | Ball |
| D335,817 S | 5/1993 | Greubel |
| 5,232,127 A | 8/1993 | Trotta et al. |
| 5,588,566 A | 12/1996 | de Laforcade et al. |
| D388,319 S | 12/1997 | Lamb |
| 5,975,377 A | 11/1999 | McGowens |
| D422,902 S | 4/2000 | Kikuchi |
| D423,922 S | 5/2000 | Ohchi et al. |
| D426,773 S | 6/2000 | Warner et al. |
| 6,264,067 B1 | 7/2001 | Lasserre |
| D449,978 S | 11/2001 | Viellard |
| D486,387 S | 2/2004 | Lee et al. |
| D490,699 S | 6/2004 | Nelson et al. |
| 6,905,049 B1 * | 6/2005 | Lambert .................. 222/321.7 |
| D508,209 S | 8/2005 | Lamb et al. |
| D508,405 S | 8/2005 | Lamb et al. |
| D508,411 S * | 8/2005 | Lamb et al. .................. D9/689 |
| D508,414 S | 8/2005 | Lamb et al. |
| D511,302 S | 11/2005 | Lamb et al. |
| D514,944 S | 2/2006 | Lamb et al. |
| 7,637,394 B2 * | 12/2009 | Grant .................. 222/182 |
| 2003/0168476 A1 | 9/2003 | Sanchez |
| 2004/0149781 A1 | 8/2004 | Kunesh et al. |
| 2005/0006416 A1 | 1/2005 | Garcia et al. |

FOREIGN PATENT DOCUMENTS

| | | |
|---|---|---|
| EP | 0513350 A1 | 11/1992 |
| EP | 1323644 | 2/2007 |
| GB | 1050339 | 3/1988 |
| GB | 2036365 | 12/1994 |
| GB | 2053750 | 7/1996 |
| GB | 2074961 | 5/1998 |
| GB | 2076728 | 12/1998 |
| GB | 3000542 | 2/2002 |
| GB | 3000546 | 2/2002 |
| RU | 2218293 | 12/2003 |
| WO | 0185573 A1 | 11/2001 |
| WO | DM/064600 | 11/2003 |
| WO | 2006018726 A1 | 2/2006 |

* cited by examiner

AEROSOL DISPENSER

CROSS REFERENCE TO RELATED APPLICATION

This application claims the benefit of U.S. Provisional Patent Application Ser. No. 60/785,611 filed Mar. 24, 2006, and PCT/US2007/064795 filed Mar. 23, 2007, the contents of which is incorporated herein by reference.

This invention relates to an aerosol dispenser which is not susceptible to being accidentally actuated. More particularly, this invention relates to an aerosol dispenser where the finger of a person must is inserted into an actuating aperture in a particular orientation to directly actuate a valve to dispense a product.

BACKGROUND OF THE INVENTION

Aerosol dispensers of various designs are prone to accidental actuation. This can be the result of the aerosol unit being pointed in the wrong direction and actuated or when mishandled prior to sale or after sale. It also can be caused with regard to personal care product aerosol dispensers where a packed travel bag is handled in a way which causes the aerosol to be actuated. This latter problem has been solved in the past through the use of a removable overcap which covers the upper dispensing part of the aerosol dispenser. However, if the removable overcap is dislodged there remains the problem of an accidental actuation.

Aerosol dispensers are comprised of a container holding the pressurized substance with a valve mechanism mounted on one end of the container. The valve mechanism has an upward extending valve stem. The valve mechanism usually is actuated by a vertical or horizontal movement of this valve stem. Mounted above the valve mechanism is a valve actuator and usually a cover for the valve actuator. The valve actuator can be comprised of the combined surface that is contacted by a person's finger and the unit that contacts and actuates the valve mechanism with a separate overcap; or it can be comprised of a combined overcap and the surface that is contacted by a persons finger with a separate unit that contacts and actuates the valve mechanism. This latter structure is described in U.S. Pat. No. 5,975,377 and in European Patent No. 1 309 500 B1. In each of these references, the cap and the finger actuator are combined into a single structure with the valve stem actuated by a separate mechanism.

U.S. Pat. No. D449,978 discloses a perfume container that has an opening in the container into which a person's finger must be placed to dispense the perfume. The actuation surface is on a lower surface of the container opening and appears to be the top of the unit that actuated the valve mechanism. The opening into which to place one's finger is the same on the front and the rear surfaces. A related design is disclosed in U.S. Pat. No. D486,387. Here, a dispenser holder has an opening into which a finger of a person is inserted to actuate a separate apparently replaceable dispenser. The actuation surface is on a lower surface. The opening is the same on the front and rear surfaces. A person's finger can be inserted from the front or rear of the dispensers. These are interesting disclosures but do not suggest the structure of the present dispenser.

The present aerosol dispenser structure precludes accidental actuation since the finger of a person must be inserted into an actuating aperture, which contains the actuating surface, in a particular orientation to actuate the dispenser to dispense the contained product. Further, it is a two piece structure. The valve actuator is comprised of the surface contacted by a person's finger and the unit that contacts the valve mechanism. This is combined with a separate structure that holds and mounts the valve actuator onto the aerosol container. There are advantages to this structure.

BRIEF DESCRIPTION OF THE INVENTION

There is provided an aerosol dispenser which is not susceptible to being accidentally actuated. Further, it directs the user to the proper orientation of the dispenser for dispensing a product. The aerosol dispenser is comprised of a body section and a dispensing section with the dispensing section at one end of the body section. The body section contains the aerosol product. An aerosol valve is located on an upper end of the body section. The dispensing section is adjacent to the upper end of the body section. The dispensing section has an enclosing unit and an actuating unit. The enclosing unit attaches the dispensing unit to the body section. The enclosing unit and the actuating unit, in a preferred embodiment, have a unitary angled front surface and a concave rear surface. The actuating unit fits into the enclosing unit to form the dispensing section.

The actuating unit has a dispensing aperture and an actuating aperture. A dispensing channel connects the aerosol valve of the body section to the dispensing aperture. The actuating aperture is sized for the insertion of a person's finger and has a flexible surface at least on a lower portion of the actuating aperture, the flexible surface comprised at least in part of a flexible material. The flexible surface can be entirely of a flexible material or can be a flexible material on a rigid to semi-rigid material that can flex. In a preferred embodiment, the flexible surface is a rigid to semi-rigid part with a flexible surface layer, the flex being provided by a cantilever attachment of the rigid to semi-rigid part to a wall of the dispenser section.

In a further preferred embodiment, the actuating aperture with angled front and concave rear surfaces extends through the dispensing section to form an actuating channel to direct a person as to the end opening of the actuating channel into which to insert a finger. The flexible surface adjacent to the valve upon being deflected downward contacts and actuates the valve on the body section to dispense the product. An upward motion of the flexible surface causes a cessation of the dispensing. This flexible surface is biased in an upward position which is the non-actuated position for the aerosol valve.

The enclosing unit is comprised of a thermoplastic and the actuating unit is comprised of a thermoplastic and an elastomer. The flexible material preferably is an elastomer.

The body section can have one or more surface recesses for gripping or decoration and will contain any one of a personal care product, a household care product, a vehicle cleaner or polish, an insecticide or insect repellant or other product. If a personal care product, it will be a product such as a deodorant or an antiperspirant, a lotion such as a suntan lotion, or a medicament to treat topical infections.

DETAILED DESCRIPTION OF THE INVENTION

The invention will be described in more detail in its preferred embodiments with reference to the drawings. However, the concepts incorporated in these preferred embodiments are susceptible to modifications, such modifications being within these described concepts.

Figure 1:
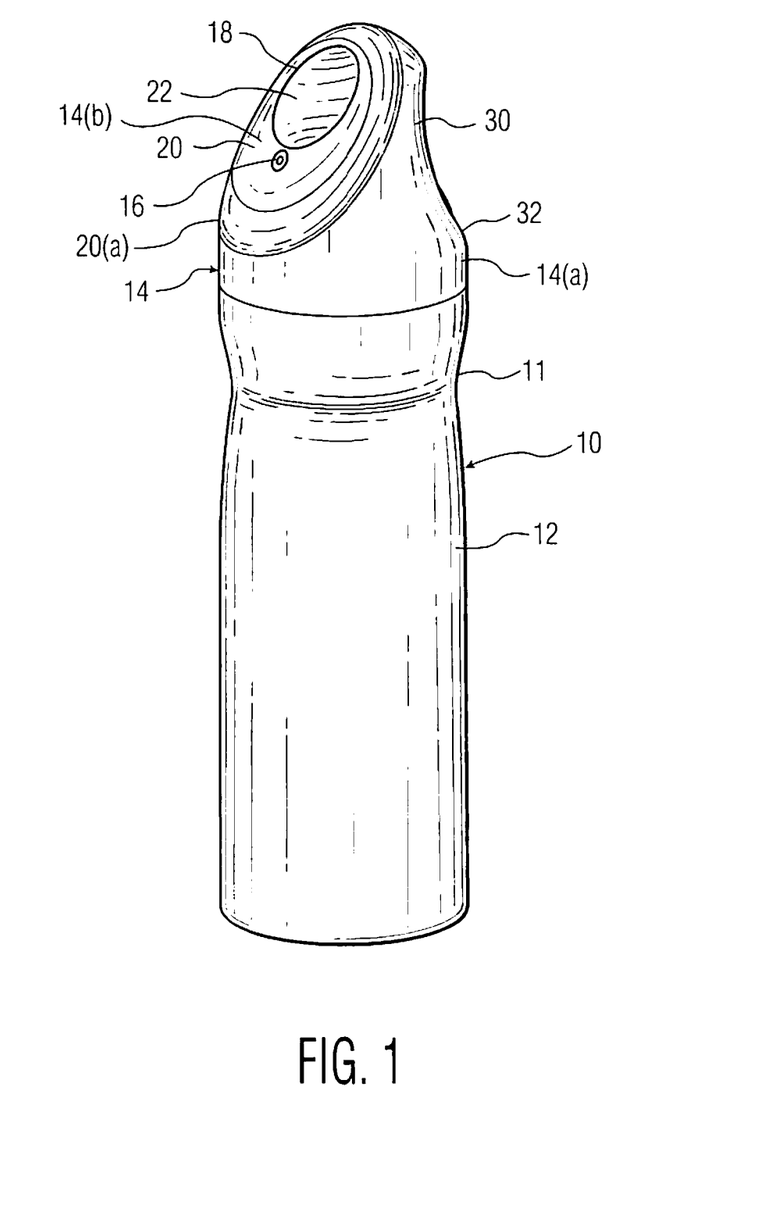
FIG. 1 is a perspective view of the aerosol dispenser.

The dispensing container 10 shown in a perspective view in FIG. 1 is comprised of a body section 12 and a dispensing section 14. The body section 12 is shown with a recessed waist portion 11 which is decorative but also will assist in the gripping of the dispensing container 10. The dispensing section has an enclosing unit 14(a) and an actuating unit 14(b) (see FIG. 6). The actuating unit 14(b) of the dispensing section 14 has a dispensing aperture 16 and an actuating aperture 18. In a preferred embodiment, the dispensing surface 20 that contains the dispensing aperture 16 is at an angle to the axis of the dispensing section. This gives the front of the dispensing section a slanting appearance. This dispensing surface 20 is shown as being angled but substantially planar but can also have a curvature. The opposite rear actuating surface 30 is concave from a lower rear surface 32 upwardly. The surface of actuating channel 22 will be flexible at least on the lower portion. The lower surface of the actuating channel 22 must flex to actuate the valve on the body section 12. In one embodiment, flexible is meant the lower surface of the actuating channel 22 can be solely of a resilient polymeric material whereby the part depressed will move upwardly and downwardly to directly actuate the valve. In another embodiment, there can be a rigid to semi-rigid portion of the inner surface of the actuation channel 22 adjacent the valve which can pivot about a pivot point, and move upwardly and downwardly. This rigid to semi-rigid portion can have a covering of a resilient polymeric material. Both embodiments are useful with the latter being a preferred embodiment. In a further preferred embodiment, the full surface of the actuating channel 22 can be of a resilient polymeric material.

Figure 2:
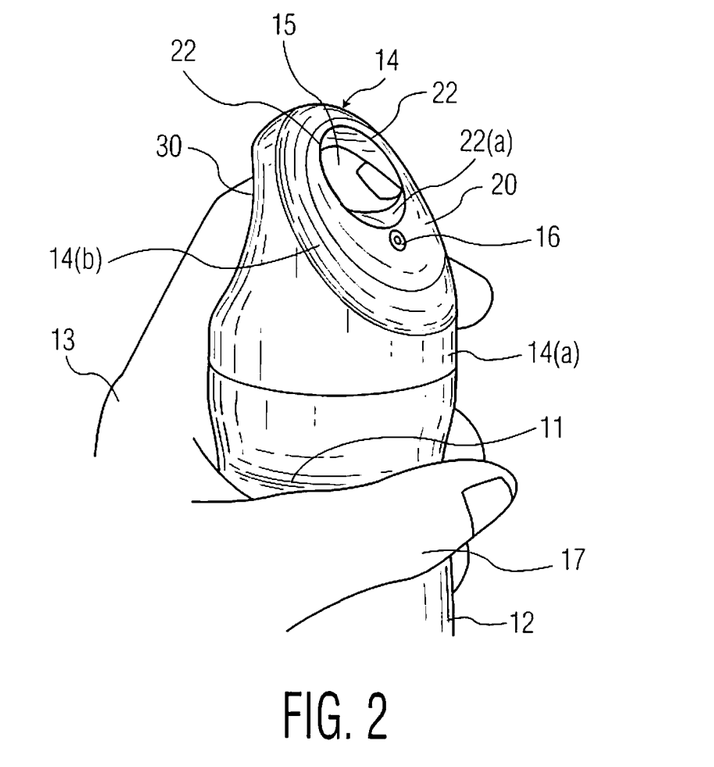
FIG. 2 is a perspective view of the aerosol dispenser of FIG. 1 in an orientation to be actuated.

FIG. 2 is a perspective view of the dispensing section 14 being actuated. Hand 13 grips the body section 12 adjacent the recessed waist 11. Finger 15 extends through the actuating channel 22 and thumb 17 grips the body section 12 of the dispensing container. Upon finger 15 depressing the lower surface 22(a) of actuating channel 22 the valve on the dispensing container will be actuated and product dispensed through dispensing aperture 16. The angled front dispensing surface 20 and the concave rear actuating surface 30 provide a visual instruction of the direction for the insertion of a person's finger.

Figure 3:
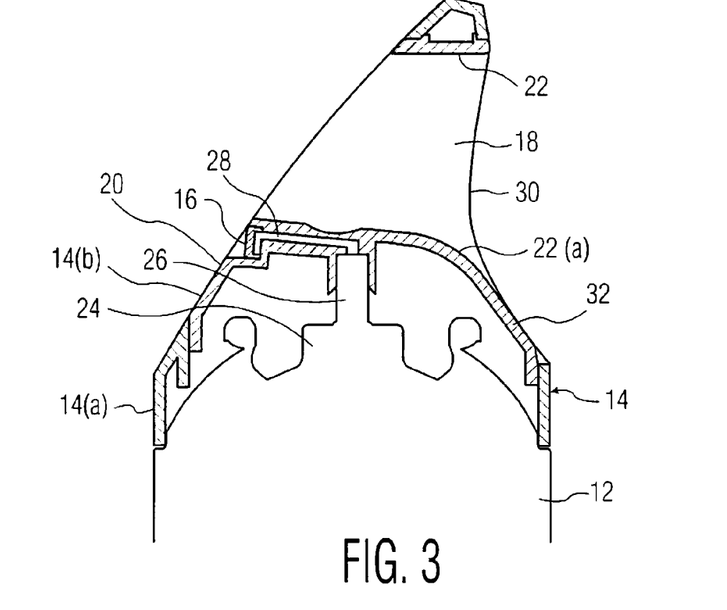
FIG. 3 is a side elevation view of the actuating unit of the aerosol dispenser in cross-section in a condition to be actuated.

FIG. 3 is a cross-sectional view of a first embodiment of the dispensing section 14 and shows the dispensing container 10 in a condition to be actuated by the finger of a user. This embodiment shows a fully flexible lower actuating surface 22(a). The finger 15 is inserted into the actuating aperture 18 and upon depressing the flexible lower actuating surface 22(a) of actuating channel 22 a valve 24 on the body section 12 is actuated and product dispensed through a valve channel 26 and a dispensing channel 28 to dispensing aperture 16. The dispensing aperture 16 is on dispensing surface 20. The rear actuating surface 30 opposite the front dispensing surface 20 is concave to better accept a person's finger. Upon a downward movement of the person's finger 15 the flexible surface 22(a) actuates the valve 24 (see FIGS. 5 to 6). The actuating channel 22 is sized to receive a finger of an average size. In this way it is of a dimension to accept a finger but will still protect the lower surface 22(a) of the actuating channel 22 from being accidentally depressed by contact with objects thus actuating the dispenser. The front surface of the enclosing unit 14(a) and the actuating unit 14(b) comprise the dispensing surface 20.

Figure 4:
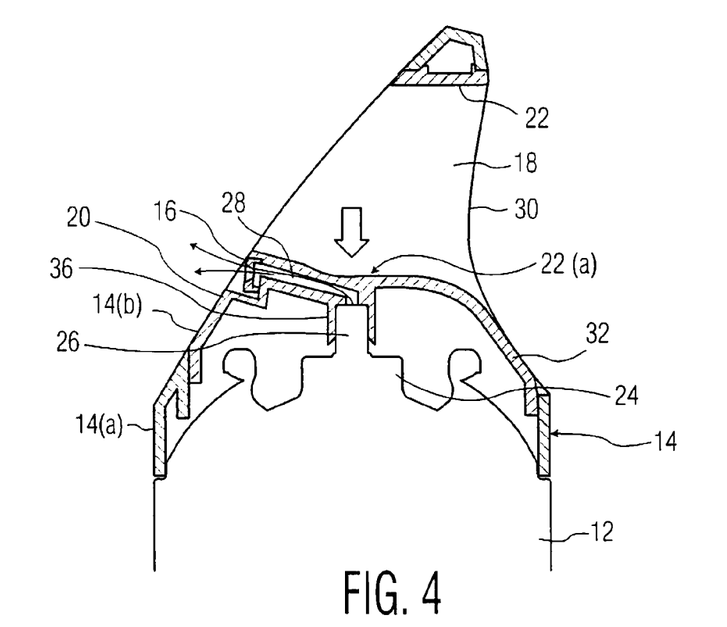
FIG. 4 is a side elevation view of the actuating unit of the aerosol dispenser in cross-section in a condition being actuated.
Figure 5:
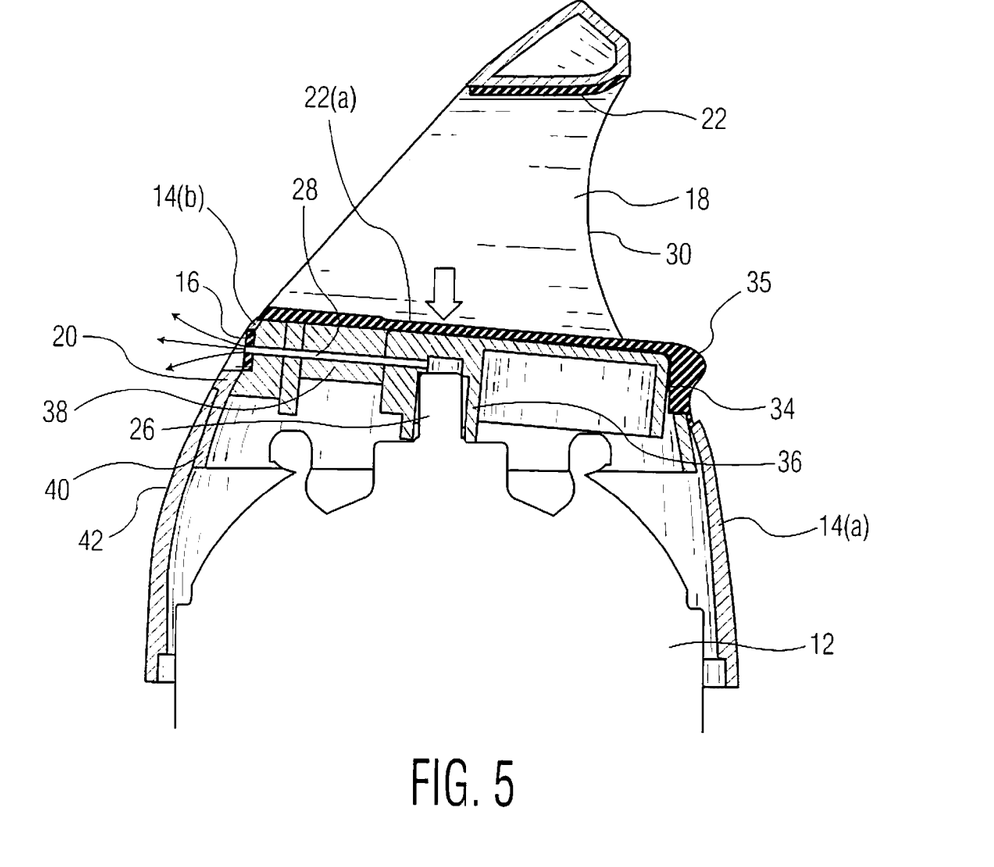
FIG. 5 is a side elevation view of the actuating unit of the aerosol dispenser in a second embodiment.

FIG. 4 shows the dispensing section 14 of FIG. 3 actuated and dispensing product from the body section 12. The body section 12 has the valve 24 with valve channel 26. The valve channel 26 communicates with dispensing aperture 16 through dispensing channel 28. The actuating aperture 18 has actuating channel 22 with at least the lower actuating surface 22(a) being flexible. The flexibility of the lower actuating surface 22(a) provides a convenient way to actuate the dispenser. An equivalent to the resilient flexibility of this surface is to have this surface comprised of a more rigid and flex and move via a hinge, being cantilevered or an equivalent structure that can deflect downward and contact the valve 24 as is shown in FIG. 5. It will then flex upward to a rest position when the dispensing force is released.

FIG. 5 is a cross-sectional view of a second embodiment of the dispensing section 14. The difference here is in the structure of the actuating channel 22 of actuating aperture 18. The body section 12 for the actuating mechanism of the embodiment of FIG. 5 will be the same as that of FIGS. 3 and 4. The dispensing section 14 parts that are the same in this FIG. 5 as those in FIGS. 3 and 4 will have the same parts numbers. In this embodiment, the actuating mechanism is comprised of rigid to semi-rigid cantilevered actuating lever 34 which usually has a flexible material covering 35. The actuator unit 34 has a valve channel 36 which accepts the valve channel 26 of the body portion. The actuating lever 34 is cantilevered from support wall 40 of the actuating unit of the dispensing section by support beam 38 which is rigidly attached to support wall 40. Upon the actuator lever 34 being depressed downwardly the support wall 40 flexes allowing the actuating lever 34 to flex downwardly and actuate aerosol valve 24. Once the actuation force on actuating lever 34 is released the wall 40 returns to its initial un-flexed position and causes the actuator lever 34 to return to its original position. The support wall 40 is separate from enclosing unit wall 42 of the dispensing section 14, but can be adjacent to wall 42. Upon the aerosol valve 24 being actuated the product flows from the aerosol valve 24 into channel 36 and through dispensing channel 28 to the dispensing aperture 16. In this embodiment the dispensing channel 28 is located in support beam 38. In order to use the aerosol dispenser a person places a finger into the concave end of the actuating channel 22 as shown in FIG. 2. This usually will be the finger adjacent to the thumb with the remainder of a person's hand gripping the container. The dispensing aperture 16 then will automatically be oriented away from the person. Pushing downward on the lower actuating surface 22(a) or 22(a)/35 will then actuate the aerosol valve 24 and the aerosol product will be dispensed.

An option in this embodiment is not to have a flexible material covering 35 on the flexible actuating lever 34. In that case the flexible material covering can be in the remainder of the actuating channel 22 but with the actuating lever moving independently of the flexible material in the remainder of the actuating channel. However, this will then leave a small gap between the actuating lever 34 and the remainder of the actuating channel 22. Although a useful option, it is not a preferred option since dust can get below the actuating lever.

In both embodiments of the dispensing container 10, the front dispensing surface 20 of the dispensing section 14 containing the dispensing aperture 16 is at an angle to the axis of the dispensing section 14 and of the body section 12. The opposite rear actuating surface 30 has a concave surface. The finger entrance lower rear surface 32 of the actuating aperture 18 extends upwardly to direct a person's finger into actuating aperture 18. These ergonomic features in combination with the shape of the dispensing aperture surface 20, and opposite concave surface 30, are designed to direct a person to properly orient the dispenser container 10.

Figure 6:
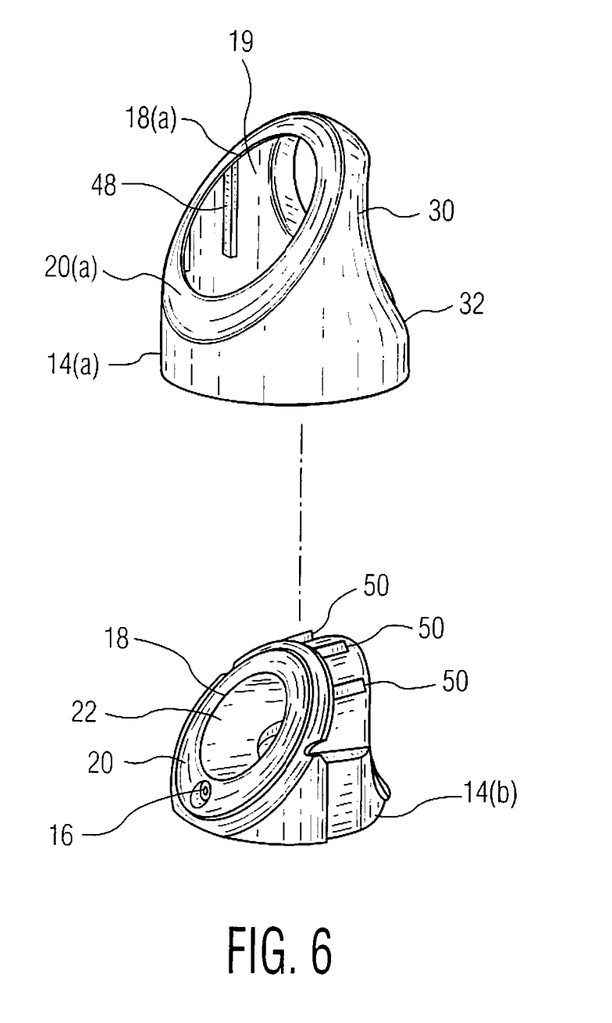
FIG. 6 is an exploded view of the dispensing section of the aerosol dispenser of FIG. 5.

FIG. 6 is an exploded view of the dispensing section 14 of the second embodiment. This view more clearly shows the two components of the dispensing section 14. There is the separate enclosing unit 14(a) and the separate actuating unit 14(b). This enclosing unit 14(a) has enclosing aperture 18(a) and enclosing front surface 20(a) of the front dispensing surface 20. Also shown are concave rear actuating surface 30 and lower rear surface 32. Inner wall 19 has a plurality of strengthening braces 48. The actuating unit 14(b) has the actuating aperture 18, actuating channel 22, front dispensing surface 20 and dispensing aperture 16. Braces 50 strengthen the structure and assist in locking the actuating unit 14(b) into enclosing unit 14(a). These two parts are assembled by inserting actuating unit 14(b) into enclosing unit 14(a).

Figure 7:
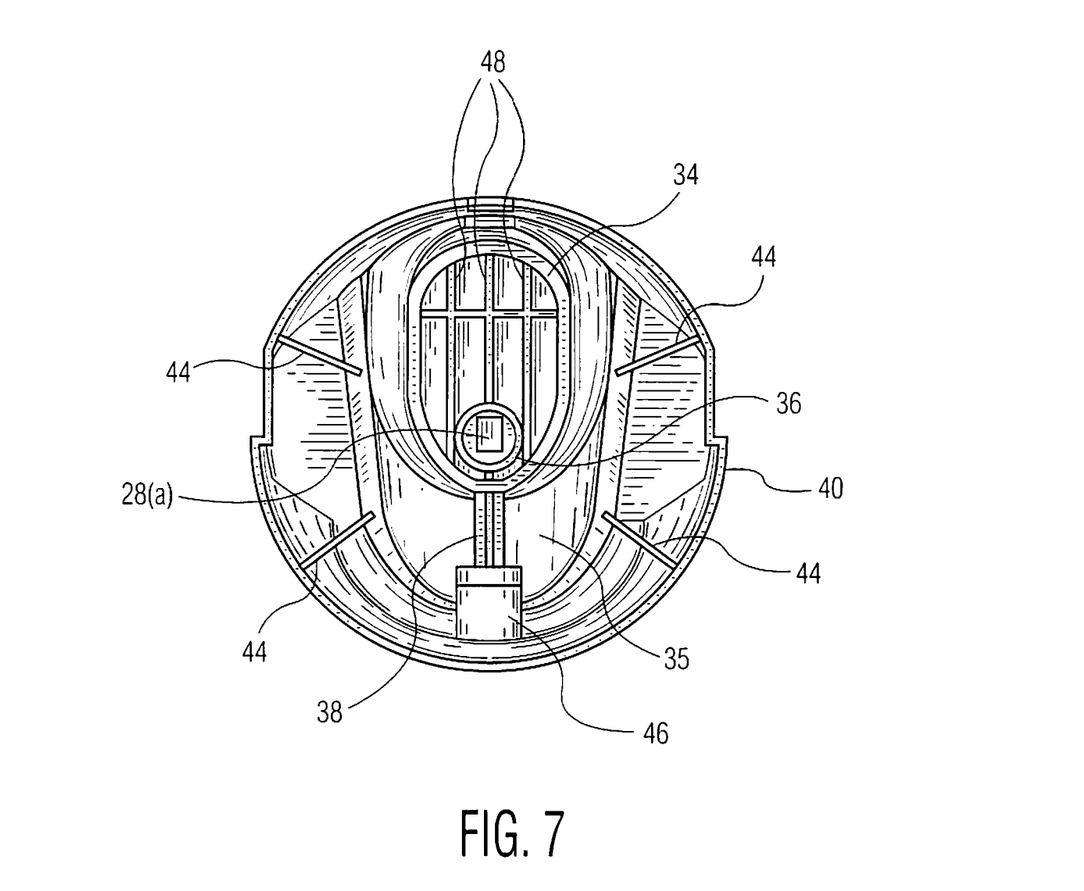
FIG. 7 is a bottom plan view of the actuating unit of FIG. 6.

FIG. 7 is a bottom plan view of the actuating unit 14(b). The peripheral support wall 40 has a plurality of structural braces 44 and a connector 46 for connecting dispenser beam 38 to support wall 40. The lower part of actuation unit 34 is shown with support braces 48 and actuator unit channel 36. The flexible material covering 35 provides a finger contact on the upper surface and a seal to the actuating unit. The valve channel 26 of the body section will extend up into actuator unit channel 36. The aperture 28(a) is the opening to dispensing channel 28. When the actuator unit 34 is depressed the actuator unit channel 36 contacts the valve channel 26 and by depressing the valve channel 26 opens valve 24 on the dispensing container 12 whereby product flows to dispensing aperture 16 and to the exterior. Depressing actuator lever 34 causes the support wall 40 to flex. Releasing the pressure on actuating lever 34 causes the support wall 40 to return to its original position and to bring actuating unit back to its original position.

Figure 8:
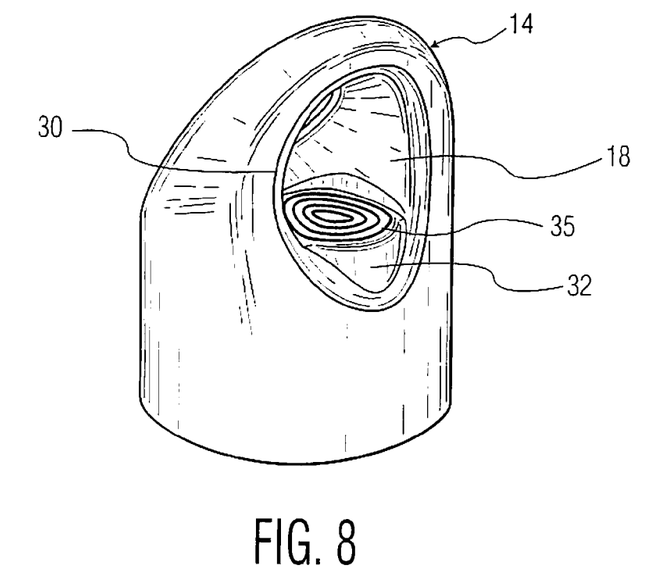
FIG. 8 is a perspective view of the dispensing section of the aerosol dispenser of FIG. 5.
Figure 9:
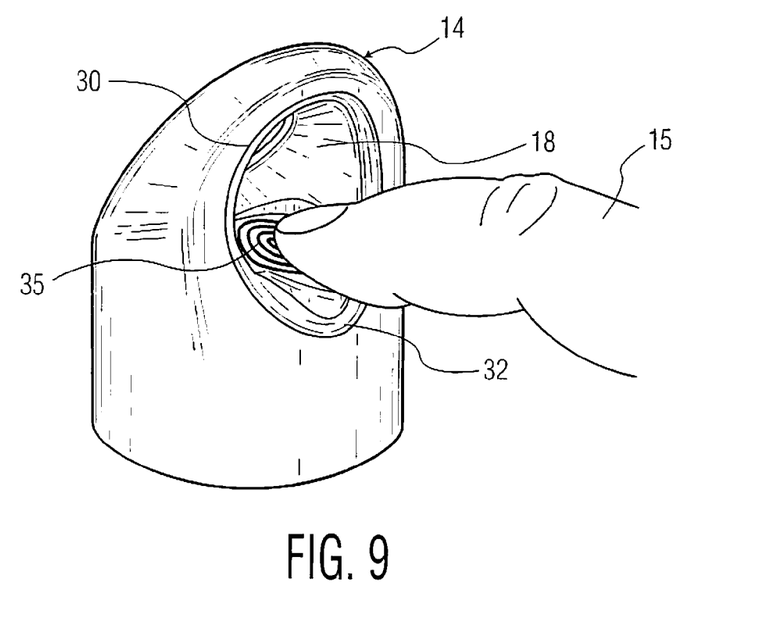
FIG. 9 is a perspective view of the dispensing section of FIG. 8 being actuated to dispense product from an aerosol dispenser.

FIG. 8 is a perspective view of the dispensing section 14 of the second embodiment. This shows the enclosing unit 14(a) and the actuating unit 14(b) of FIG. 6 fully assembled and ready for use. There is seen in FIG. 8 the concave rear actuating surface 30 with actuating aperture 18 and flexible material 35 covering actuation lever 34. The flexible lower rear surface 32 will flex when the flexible material 35 actuating lever 34 are depressed. FIG. 9 shows the dispensing section of FIG. 8 being actuated by depressing flexible material surface 35 by means of finger 15.

The container body 12 can contain essentially any personal care product, a household care product, a vehicle cleaner or polish, room deodorizer, fabric treatment, an insecticide or repellant or other product that is susceptible to aerosol dispensing. In the personal care area, this will include hair care products, lotions such as sun tan lotions, antiperspirants and deodorants, room deodorizers, fabric treatment, and medicaments to treat topical infections. In the household care area, this will include various cleaning and disinfecting products. In essence, this aerosol dispenser can be used to dispense essentially any product that is usually dispensed as an aerosol.

The container body 12 can be comprised of a metal or plastic. The container body can be comprised of aluminum or steel alloys. It can be of essentially any shape, and if metal, can be made by conventional can making equipment and processes. If plastic it can be made by conventional injection molding or blow molding processes. The valve on the container can be a commonly used aerosol valve such as those available from the Precision Valve Corporation. 700 Nepperhan Avenue, Yonkers, N.Y., United States of America, or from Lindal Vental Gmbh, Industriestr 13. D-23843 Bad Oldesolve, Germany. The dispensing section 14, inclusive of the enclosing unit 14(a) and the actuating unit 14(b), is usually plastic and is injection molded. The actuating channel 22 of the dispenser section can likewise be injection molded and then assembled onto the molded dispensing section 14 of the closure. In addition the dispensing section 14 and the actuating channel 22 can be bi-injection molded in a single mold and a two injection molding step. The plastic of the dispenser section can be any thermoplastic such as any polymer or copolymer of ethylene, propylene, styrene and vinyl monomers. Useful thermoplastics are polyethylenes and polypropylenes. However, essentially any other thermoplastic can be used. The rigid to semi-rigid material of the actuating lever 34 likewise will be one of the same thermoplastics.

The inner surface of the actuating channel 22 preferably will be resilient, and preferably will be a pliable, elastomeric rubberlike material. It can be a thermoplastic elastomer or a subclass of thermoplastic vulcanates. Such elastomers are available from the ExxonMobil Chemical Company under the product names Santoprene, Vyram, Geoplast, Vistaflex and Dytron. It will be moldable to the desired shape to be fitted into the more rigid structure of the dispensing section 14 of the dispenser container 10 or it can be bi-injection molded along with the more rigid dispensing section 14 structure. In addition this material can be a silicone or a natural or synthetic rubber. In the embodiment where the actuating lever 34 is rigid to semi-rigid essentially any thermoplastic can be used. These include the above described polymers and copolymers. The flexible material 35 covering actuating lever 34 be any can be any of the above described elastomers.

We claim:

1. An aerosol container comprising a body section and a dispensing section, the body section comprising a container having an aerosol valve at one end, the dispensing section comprising an enclosing unit and an actuating unit, the actuating unit adjacent the aerosol valve of the body section, the enclosing unit attaching the actuating unit to the body section, the actuating unit having a dispensing aperture and an actuating aperture, the actuating aperture sized to receive a finger of a person, the dispensing aperture in communication with the aerosol valve, the actuating aperture extending through said dispensing section to form an actuating channel, the actuating channel having opposing open ends, at least a lower portion of said actuating channel being flexible and in direct contact with the aerosol valve on the body section to thereby actuate the aerosol valve when the lower portion of said actuating channel is depressed, wherein the actuating unit is comprised of a thermoplastic and an elastomer.

2. The aerosol container of claim 1, wherein each of the enclosing unit and the actuating unit have an aperture sized to receive the finger of a person, the actuating unit fitting within the enclosing unit to form the dispensing section and a unitary actuating aperture.

3. The aerosol container of claim 1, wherein the lower portion of the actuating channel is comprised of a flexible material.

4. The aerosol container of claim 3, wherein more than the lower portion of the actuating channel is comprised of a flexible material.

5. The aerosol container of claim 1, wherein the dispensing aperture is located below the actuating aperture.

6. The aerosol container of claim 1, wherein the lower portion of the actuating channel is comprised of a flexing rigid to semi-rigid material, the flexing rigid to semi-rigid material attached to a support wall, the support wall flexing when the flexible material on the upper surface of the flexing rigid to semi-rigid material is depressed to thereby actuate the aerosol valve.

7. The aerosol container of claim 6, wherein the flexing rigid to semi-rigid material has a covering of a flexible material.

8. The aerosol container of claim 6, wherein the rigid to semi-rigid material is cantilevered from the support wall adjacent to the dispensing aperture.

9. The aerosol container of claim 8, wherein the support wall is at the periphery of the actuator unit.

10. The aerosol container of claim 6, wherein the dispensing aperture is located below the actuating aperture.

11. The aerosol container of claim 1, wherein said dispensing section has a rear surface that is concave and a front dispensing surface that is at an angle to the axis of the dispensing section.

12. The aerosol container of claim 2, wherein said dispensing section has a rear surface that is concave and a front dispensing surface that is at an angle to the axis of the dispensing section.

13. The aerosol container of claim 6, wherein said dispensing section has a rear surface that is concave and a front dispensing surface that is at an angle to the axis of the dispensing section.

14. The aerosol container of claim 1, wherein said actuating channel of the actuating unit is comprised of an elastomer on the inner surface of a thermoplastic forming the actuating channel.

15. The aerosol container of claim 1, wherein said actuating channel of the actuating unit is comprised of an elastomer.

16. The aerosol container of claim 15, wherein said elastomer is selected from a synthetic rubber, a natural rubber or a combination of a natural rubber and a synthetic rubber.

* * * * *